US006335471B1

(12) United States Patent
Eastham et al.

(10) Patent No.: US 6,335,471 B1
(45) Date of Patent: Jan. 1, 2002

(54) METHOD OF MANUFACTURING PHOSPHINE COMPOUND

(75) Inventors: Graham Ronald Eastham, Durham; Jamie Michael Thorpe; Robert Paul Tooze, both of Cleveland, all of (GB)

(73) Assignee: Ineos Acrylics UK Limited, Hampshire (GB)

( * ) Notice: Subject to any disclaimer, the term of this patent is extended or adjusted under 35 U.S.C. 154(b) by 0 days.

(21) Appl. No.: 09/485,470
(22) PCT Filed: Aug. 7, 1998
(86) PCT No.: PCT/GB98/02392
    § 371 Date: Apr. 13, 2000
    § 102(e) Date: Apr. 13, 2000
(87) PCT Pub. No.: WO99/09040
    PCT Pub. Date: Feb. 25, 1999

Related U.S. Application Data

(60) Provisional application No. 60/061,627, filed on Oct. 9, 1997.

(30) Foreign Application Priority Data

Aug. 13, 1997 (GB) .............................. 9717059

(51) Int. Cl.$^7$ ................................. C07F 9/50
(52) U.S. Cl. .............................. 568/17; 568/8
(58) Field of Search ................ 568/8, 13, 16, 568/17

(56) References Cited

U.S. PATENT DOCUMENTS 4,774,362 A * 9/1988 Devon et al.

FOREIGN PATENT DOCUMENTS

WO         96/19434         6/1996

OTHER PUBLICATIONS

CA:111:134423 abs of J Chem Soc Chem Commun by Carr et al (14) pp. 926–928, 1988.*
CA:114:43147 abs of Organometallics by Mole et al 10(1) pp. 49–52, 1991.*
CA:88:136727 abs of Helv Chim Acta by Kapoor et al 60(8) pp. 2824–2829, 1977.*

Belstein 2864439 abs of J Chem Soc Dalton Trans by Moulton pp. 1020–1023, 1976.*

J. C. S. Dalton, 1979, "Formation of . . . Rings" by Najeeb a–Al–Salem et al., pp. 1972–1982.

J. C. S. Dalton, 1980, "Formation of . . . Rings" by Najeeb A. Al–Saleem et al., pp. 59–63.

Organometallics 1997, 16, 3786–3793, publication date Aug. 19, 1997 "Unexpected . . . Donor" by Boris Rybtchinski et al.

Chemical Abstracts, vol. 96 1992, pp. 1–3.

* cited by examiner

Primary Examiner—Jean F. Vollano
(74) Attorney, Agent, or Firm—Pillsbury Winthrop LLP

(57) ABSTRACT

A method of preparing a compound (I) of general formula $(R_3-C)_2P-L^1-X-L^2-P-(C-R_3)_2$, in which R is independently a pendant, optionally substituted, organic group through which the group is linked to tertiary carbon atoms C; $L^1$ and $L^2$ are independently, a linking group selected from an optionally substituted lower alkylene chain connecting the respective phosphorous atom to the group X, and X is a bridging group comprising an optionally substituted aryl moiety to which the phosphorous atoms are linked on available adjacent carbon atoms; comprising: (i) reacting together a compound (II) of formula $A-L^1-X-L^2-A$, in which A is a halogen atom, with a metal M in a suitable solvent or form an intermediate compound (III) of formula: $A-M-L^1-X-L^2-M-A$; (ii) reacting said intermediate compound (III) with a compound (IV) of formula: $(R_3-C)_2P-A^1$, wherein $A^1$ is a halogen atom which may be the same as or different from A, to form said compound (I).

6 Claims, No Drawings

METHOD OF MANUFACTURING PHOSPHINE COMPOUND

This application is the national phase of international application PCT/GB98/02392 filed Aug. 7, 1998 which designated the U.S.

This application also claims the benefit of U.S. Provisional Application No. 60/061,627, filed Oct. 9, 1997.

The present invention relates to a phosphine compound which is useful as a component of a catalyst system which may be used in the carbonylation of olefins, and in particular to a method of manufacturing such phosphine compounds.

WO 96/19434 discloses a process for the carbonylation of ethylene and a catalyst system for use therein. The catalyst system described in that document comprises a bidentate phosphine ligand of general formula $(R_3-C)_2P-L^1-X-L^2-P-(C-R_3)_2$, in which each R is independently a pendant, optionally substituted, organic group through which the group is linked to tertiary carbon atom C; $L^1$, $L^2$ are independently a linking group selected from an optionally substituted lower alkylene chain connecting the respective phosphorous atom to the group X and X is a bridging group comprising an optionally substituted aryl moiety to which the phosphorous atoms are linked on available adjacent carbon atoms; and a Group VIII metal or compound thereof. One example of such a bidentate phosphine ligand is bis(di-$^t$butyl phosphino)-o-xylene.

Such catalysts may be made by mixing the phosphine ligand with a suitable source of palladium such as palladium acetate. WO 96/19434 describes the preparation of one form of the ligand via the phosphonium salt produced from the reaction of the appropriate secondary phosphine with the corresponding aromatic dihalide. In the preferred form of the phosphine ligand in WO 96/19434, R is a lower alkyl group, in particular methyl. A problem with manufacturing this ligand by the route described is that the secondary phosphine which is used (e.g. di-$^t$butyl phosphine) is toxic, highly reactive, smelly and flammable. We have also found that the reaction is low yielding and converts some of the di-$^t$butyl phosphine to a non-reclaimable waste product which must be disposed of.

Zvezdina et al (VINITI 3581-80, Chemical Abstracts Vol 96 (1992) 52409) describe a method of forming 1,2-ethynediylbis[bis(1-methylethyl)phosphine] by reaction of dibromoethynyidimagnesium with di-isopropyl chlorophosphine to produce ligands for hydroformylation catalysts.

A paper by M. F. Lappert & T. R. Martin (J. Chem. Soc., Dalton Trans., 1982 p1952) describes the preparation of various metallocyclic compounds via a di-Grignard synthesis route.

We have now found that phosphine ligands of the type described in WO 96/19434 may be prepared by a high yielding route using more benign materials which produce less waste product than the route described in WO 96/19434.

According to the invention, a method of manufacturing a compound of general formula $(R_3-C)_2P-L^1-X-L^2-P-(C-R_3)_2$ (I), in which each R is independently a pendant, optionally substituted, organic group through which the group is linked to tertiary carbon atom C; $L^1$, $L^2$ are independently a linking group selected from an optionally substituted lower alkylene chain connecting the respective phosphorous atom to the group X and X is a bridging group comprising an optionally substituted aryl moiety to which the phosphorous atoms are linked on available adjacent carbon atoms comprises the steps of i) reacting together a compound of formula $A-L^1-X-L^2-A$ (II), in which A is a halogen atom, with a metal M in a suitable solvent to form an intermediate compound of formula $A-M-L^1-X-L^2-M-A$ (III), ii) reacting said intermediate compound (III) with a compound of formula $(R_3-C)_2P-A^1$ (IV), where $A^1$ is a halogen atom which may be the same as or different from A, to form said compound (I).

The compound (I) of general formula $(R_3-C)_2P-L^1-X-L^2-P-(C-R_3)_2$ may be useful as a component of a catalyst compound. In particular WO 96/19434 describes the use of such compounds as bidentate ligands which, when used together with a Group VII metal such as palladium, are effective catalysts for the carbonylation of olefins.

The pendant, optionally substituted organic groups, R may be independently selected from a wide range of components. Preferably, the pendant groups are optionally substituted lower alkyl, e.g. $C_{1-8}$, and may be branched or linear. Each R group may be the same as or different from each other R group. It is preferred that $(R_3-C)_2P-L^1-X-L^2-P-(C-R_3)_2$ is symmetrical in that both $(C-R_3)_2$ groupings are the same.

Particularly preferred is when the organic groups, R, when associated with their respective carbon atom, form composite groups which are at least as sterically hindering as tert-butyl. Steric hindrance in this context is as discussed at page 14 et seq of "Homogeneous Transition Metal Catalysis—A Gentle Art", by C Masters, published by Chapman and Hall, 1981.

The linking groups, $L^1$ and $L^2$, are independently selected from an optionally substituted, particularly lower alkyl, e.g. $C_1$ to $C_4$, substituted, lower alkylene, e.g. $C_1$ to $C_4$ chain. Especially preferred is when both $L^1$ and $L^2$ are methylene.

The bridging group X is an aryl moiety, e.g. a phenyl group, which may be optionally substituted, provided that the two phosphorus atoms are linked to adjacent carbon atoms, e.g. at the 1 and 2 positions on the phenyl group. Optional substitution of the aryl moiety may be by other organic groups, e.g. alkyl, particularly $C_{1-8}$, aryl, alkoxy, carbalkoxy, halo, nitro, trihalomethyl and cyano. Furthermore, the aryl moiety may be a fused polycyclic group, e.g. naphthalene, biphenylene or indene.

Examples of compounds (I) which may advantageously be made by the method according to the invention are described in WO 96/19434, which is incorporated herein by reference, and include bis(di-tert-butyl phosphino)-o-xylene (also known as 1,2 bis(di-tert-butylphosphinomethyl) benzene), bis(di-t-neopentyl phosphino)-o-xylene and bis 1,2 (di-tert-butyl phosphino)naphthalene.

M may be any suitable metal which forms a polar organometallic group on reaction with an alkyl halide. Suitable metals include those of Group II and Group IIB, e.g. magnesium, calcium, zinc, cadmium, mercury, aluminium, gallium, indium, tin and lead. The preferred metal is magnesium. When magnesium is used, the compound (III) is known as a di-Grignard compound. The magnesium may be in any convenient form such as turnings, chips, granules, ribbon etc, but it is preferred to use magnesium powder.

The nature of the compound (II) is dependent upon the nature of the product compound (I) which is required. When the $L^1$ and $L^2$ are both methylene groups and X is an unsubstituted phenyl group, the preferred starting material is α,α' dichloro-o-xylene. A is a halogen atom. The preferred halogen is chlorine although other halogens, e.g. bromine may be effective.

We have found that the compound (II) is beneficially added to the metal gradually, e.g. dropwise or by use of another means for achieving a slow addition, e.g. a controllable pump.

The formation of di-Grignard compounds, e.g. o-$C_6H_4$ $(CH_2MgCl)_2$, is described by M. F. Lappert et al in J. Chem Soc. Dalton Trans. (1982) p.1959. This paper describes the preparation of metallocyclic compounds via a di-Grignard reaction, but the practical preparation of di-Grignard compounds is well described and may be useful in the preparation of compound (III) of this invention. Thus, following the teaching of this document, which is incorporated herein as a reference, the yield of a di-Grignard compound may be increased if THF is used as a solvent and when the concentration of the compound (II) and thus of a resulting di-Grignard compound (III) in the solvent is relatively low, e.g. less than about 0.1 mole/l, preferably of the order of about 0.075 mole/l.

The nature of the phosphine compound (IV) is dependent upon the product compound to be prepared. The pendant, optionally substituted organic groups, R may be independently selected from a wide range of components. Preferably, the pendant groups are optionally substituted lower alkyl, e.g. $C_{1-8}$, and may be branched or linear. Each R group may be the same as or different from each other R group. It is preferred that $(R_3-C)_2P-L^1-X-L^2-P-(C-R_3)_2$ is symmetrical in that both $(C-R_3)_2$ groupings are the same. $A^1$ is preferably a chlorine or bromine or iodine atom. As an example, when each R group is a methyl group, i.e. when $(C-R_3)_2$ is t-butyl, then the phosphine compound (IV) may be di t-butylchlorophosphine. The compound (IV) may be obtained by synthesis, e.g. via a Grignard reaction in which $(R_3-C)MgCl$ is reacted with $PCl_3$ or by other synthetic methods known in the art. Some suitable materials may also be available commercially.

The phosphine compound (IV) may be added to the compound (III) at amounts in excess of the stoichiometric amount required. Preferably the ratio of compound (IV) to compound (III) is at least 2:1, although faster reaction rates can be achieved if the ratio is greater, e.g. at least 4:1. However, the increase in the rate of reaction achieved at these higher ratios must be offset by the economics of using more phosphine compound. Usually the ratio of compound (IV) to compound (III) would be less than 20:1, preferably less than about 10:1.

The solvent used must not contain any component which reacts with the intermediate compound, and suitable such solvents will be well known to the skilled chemist. Favoured solvents include dry etheric solvents such as tetrahydrofuran (THF), dioxane and dimethoxyethane. The preferred solvent is THF. The formation of a di-Grignard compound must be carried out in dry conditions because water reacts with the Grignard compound to produce $H-L^1-X-L^2-H$ in a side reaction.

The reaction between compound (III) and Compound (IV) may be heated to increase the rate of reaction, if required. However, if the reaction is particularly rapid, the reaction may be more easily controlled in the absence of additional heat or with cooling. The reduction of the rate of reaction in this way may be beneficial in reducing side reactions in certain systems. As an example, we have found that when compound (IV) is a chlorophosphine the reaction may be easily controlled and a satisfactory rate achieved if heated slightly, e.g. the reaction is carried out at a temperature of about 50° C. However, when the corresponding bromophosphine is used instead of the chlorophosphine, the reaction may be very rapid at room temperature and thus no additional heat is needed and cooling the reaction mixture may be advantageous.

The compound (I) may be isolated from the reaction mixture by distilling off the excess solvent and excess reactants if present, preferably under vacuum, and then extracting the product compound into a solvent, e.g. hexane or methanol (preferably hot), from which it may be precipitated or recrystallised. Other techniques and reagents for isolating the product available to those skilled in the art of organic chemistry may be found to be suitable.

The invention will be further described, by way of example only, below.

EXAMPLE 1

Preparation of Compound (III)

1.35 g (55 mmol) of powdered magnesium was activated by heating at 90° C. under vacuum for 30 minutes, followed by cooling and stirring with a single crystal of iodine, in about 40 ml of THF which had been previously distilled under $N_2$ over sodium, until the iodine stain was removed. The solution of magnesium iodide was filtered off and the metal resuspended in about 40 ml distilled THF. To this was added 2.42 g (13.8 mmol) of sublimed α,α'-dichloro-ortho-xylene as a solution in THF (140 ml) over a period of 3–4 hours and the reaction mixture stirred overnight. The resulting solution of di-Grignard solution was filtered and quenched with 2 ml of degassed water to produce ortho-xylene. The ortho-xylene produced was then analysed by gas chromatography, and compared with standard solutions made up in the laboratory to determine the yield. The yield was estimated to be 91% based on α,α'-dichloro-ortho-xylene starting material, confirming that the reaction produces a high yield of the di-Grignard compound.

EXAMPLE 2

Example 1 was repeated except that α,α'-dibromo-ortho-xylene was used instead of the dichloro compound of Example 1. The yield was determined to be 15%. This reduced yield compared with Example 1 is probably due to the increased reactivity of the bromide di-Grignard promoting rapid coupling of the Grignard molecules.

EXAMPLE 3

Preparation of Compound (I)

A di-Grignard compound was made from α,α'-dichloro-ortho-xylene and magnesium powder, as described in Example 1. The yield of di-Grignard was determined by GC analysis of a water quenched sample of the filtered reaction mixture to be 94%. The resulting filtered di-Grignard compound was functionalised by adding the di-Grignard dropwise to a vigorously stirred THF solution of a two-fold excess of di-tert-butylchlorophosphine (as supplied by from Aldrich) which was then refluxed for 8 hours after the addition was complete. The yield of bis(di-tert-butyl phosphino)-o-xylene was determined by $^{31}P$ nuclear magnetic resonance to be 55% based on the di-Grignard present. A number of other unidentified phosphorous-containing compounds were also found in the reaction mixture.

EXAMPLE 4

Variation of the Ratio of Compound (IV): Compound (III)

6.73 g (0.277 moles) of magnesium powder was activated using a single crystal of iodine in 125 ml of distilled THF. 12.11 g (0.069 moles) of α,α'-dichloro-ortho-xylene in 875 mls of distilled THF was added dropwise to the magnesium mixture over a period of 4 hours, using a Gilson pump to control the rate of addition, and the mixture was stirred overnight. The resulting di-Grignard solution was filtered and a small sample quenched with water in order to determine the yield by gas chromatography analysis for orthoxylene. The di-Grignard compound was then added to di-t- butylchlorophosphine in varying proportions as shown in Table 1 and stirred for up to about 24 hrs at 50° C. The reaction end-point was determined by $^{31}$P NMR to monitor the formation of product. The solvent was removed under vacuum and the resulting waxy solid was recrystallised from hot methanol. The yield was calculated based on di-Grignard and is shown in Table 1.

TABLE 1

|  | 2:1 phosphine: diGrinard | 4:1 phosphine: diGrinard | 8:1 phosphine: diGrignard |
|---|---|---|---|
| yield of bis (di-tert-butyl phosphino)-o-xylene | 42.8 | 55.3 | 61.8 |

EXAMPLE 5

A di-Grignard compound was made from α,α'-dichloro-ortho-xylene and magnesium powder, as described in Example 1 and added to a solution of a mixture comprising 80% w/w of di-t-butylbromophosphine and 20% w/w di-t-butylchlorophosphine. The reaction was monitored by $^{31}$P NMR analysis of samples extracted from the mixture to monitor the formation of product as time progressed. The amount of the bromophosphine in the mixture was very rapidly reduced with the consequent rapid formation of bis(di-tert-butyl phosphino)-o-xylene product, and the level of the chlorophosphine reduced much more slowly. Therefore the bromophosphine reacted more rapidly than the chlorophosphine to give the desired product, The bromophosphine was not detected in the mixture after about 8 hours, whereas some chlorophosphine remained after 24 hrs. The yield of product was 23% based on the di-Grignard reactant.

We claim:

1. A method of making a compound represented by formula (I)

$$(R_3\text{---}C)_2P\text{---}L^1\text{---}X\text{---}L^2\text{---}P\text{---}(C\text{---}R_3)_2$$

comprising:

a) reacting a compound represented by formula (III)

$$A\text{---}L^1\text{---}X\text{---}L^2\text{---}A \quad (III)$$

with a metal M in a suitable solvent to form an intermediate compound represented by The following formula $$A\text{---}M\text{---}L^1\text{---}X\text{---}L^2\text{---}M\text{---}A$$

and b) reacting said intermediate compound with a compound represented by the formula (IV)

$$(R_3\text{---}C)_2P\text{---}A^1 \quad (IV)$$

wherein:
A and $A^1$ independently represent a halogen atom;
$L^1$ and $L^2$ are independently linking groups selected from an optionally substituted lower alkylene chain;
X is a bridging group consisting essentially of an optionally substituted aryl moiety to which the said linking groups are bound through adjacent carbon atoms of the aryl moiety; and
R is independently a pendant, optionally substituted, organic group.

2. The method as claimed in claim 1, wherein M is magnesium.

3. The method of claim 1 wherein A is chlorine.

4. The method of claim 1 wherein $A^1$ is a chlorine, bromine, or iodine atom.

5. The method of claim 1 wherein each R group is, independently, an alkyl radical.

6. The method of claim 1 wherein compound (I) is selected from the group consisting of bis(di-tert-butyl phosphino)-o-xylene, bis(di-t-neopentyl phosphino)-o-xylene and bis 1,2(di-tert-butyl phosphino)naphthalene.

* * * * *